United States Patent
Bleunven et al.

(10) Patent No.: US 12,064,187 B2
(45) Date of Patent: Aug. 20, 2024

(54) METHOD AND SYSTEM FOR COMPUTER GUIDED SURGERY

(71) Applicant: GANYMED ROBOTICS, Paris (FR)

(72) Inventors: Blaise Bleunven, Paris (FR); Cyril Moulin, Argonay (FR); Sophie Cahen, Paris (FR); Nicolas Loy Rodas, Puteaux (FR); Michel Bonnin, Lyons (FR); Tarik Ait Si Selmi, Lyons (FR); Marion Decrouez, Sèvres (FR)

(73) Assignee: GANYMED ROBOTICS, Paris (FR)

( * ) Notice: Subject to any disclaimer, the term of this patent is extended or adjusted under 35 U.S.C. 154(b) by 468 days.

(21) Appl. No.: 17/606,258

(22) PCT Filed: Apr. 24, 2020

(86) PCT No.: PCT/EP2020/061522
§ 371 (c)(1),
(2) Date: Oct. 25, 2021

(87) PCT Pub. No.: WO2020/216934
PCT Pub. Date: Oct. 29, 2020

(65) Prior Publication Data
US 2022/0296302 A1    Sep. 22, 2022

(30) Foreign Application Priority Data

Apr. 26, 2019 (FR) .................................... 1904453

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/00* (2016.02); *A61B 34/20* (2016.02); *A61B 34/30* (2016.02);
(Continued)

(58) Field of Classification Search
CPC ......... A61B 34/30; A61B 34/37; A61B 34/35; A61B 34/70; A61B 2034/305;
(Continued)

(56) References Cited

U.S. PATENT DOCUMENTS 10,136,950 B2    11/2018    Schoenefeld
2016/0045317 A1    2/2016    Lang et al.
(Continued)

FOREIGN PATENT DOCUMENTS

JP    05-011689 A    1/1993
JP    2001-293007 A    10/2001
(Continued)

OTHER PUBLICATIONS

Search Machine Translation of WO 03/088143 A2 to Haigron et al., Method for Assisting and Guiding the Navigation of a Tool in Anatomical Structures, translated Mar. 12, 2024, 48 pages. (Year: 2024).*

(Continued)

*Primary Examiner* — Matthew C Bella
*Assistant Examiner* — Dennis Rosario
(74) *Attorney, Agent, or Firm* — Morgan, Lewis & Bockius LLP

(57) ABSTRACT

A computer-implemented method and a system for computer guided surgery, which include a transposition of an action, planned in a virtual environment with respect to a virtual referential $R_P$, to a physical action performed with a surgical tool in a real operating theatre environment for orthopedic surgery of a patient.

20 Claims, 11 Drawing Sheets

(51) Int. Cl.
- *A61B 34/20* (2016.01)
- *A61B 34/30* (2016.01)
- *A61B 90/00* (2016.01)
- *A61B 90/50* (2016.01)
- *G06T 3/14* (2024.01)
- *G06T 7/33* (2017.01)
- *G06T 7/38* (2017.01)

(52) U.S. Cl.
CPC .............. *A61B 90/36* (2016.02); *A61B 90/50* (2016.02); *G06T 3/14* (2024.01); *G06T 7/344* (2017.01); *G06T 7/38* (2017.01); *A61B 2034/105* (2016.02); *A61B 2034/107* (2016.02); *A61B 2034/2055* (2016.02); *A61B 2034/252* (2016.02); *A61B 2090/365* (2016.02); *A61B 2090/3983* (2016.02)

(58) Field of Classification Search
CPC ........ A61B 2034/302; A61B 2034/303; A61B 34/00; A61B 34/10; A61B 2034/101; A61B 2034/102; A61B 2034/104; A61B 2034/105; A61B 34/20; A61B 2034/2057; A61B 2034/2065; A61B 2034/107; A61B 2090/3983; A61B 1/00097; A61B 2090/364; A61B 2034/2046; A61B 2090/365; A61B 1/00194; A61B 2017/00022; A61B 1/00087; A61B 18/1477; A61B 18/14; A61B 18/1402; A61B 2576/00; A61B 6/4458; Y10T 74/20305; Y10S 901/00; Y10S 901/46; Y10S 901/47; G06T 3/14; G06T 7/344; G06T 7/38; G06T 7/37; G06T 7/30; G06T 2207/30004; G06T 2207/30012; G06T 2207/30008

See application file for complete search history.

(56) References Cited

U.S. PATENT DOCUMENTS

| | | |
|---|---|---|
| 2017/0333137 A1 | 11/2017 | Roessler |
| 2018/0014891 A1 | 1/2018 | Krebs et al. |
| 2018/0235715 A1 | 8/2018 | Amiot et al. |
| 2019/0142524 A1 | 5/2019 | Hladio et al. |
| 2019/0201155 A1 | 7/2019 | Gupta et al. |
| 2023/0181264 A1 | 6/2023 | Kang et al. |
| 2023/0355312 A1* | 11/2023 | Bleunven ............... A61B 90/50 |

FOREIGN PATENT DOCUMENTS

| | | | |
|---|---|---|---|
| JP | 2008-502396 A | | 1/2008 |
| JP | 2019-519257 A | | 7/2019 |
| JP | 2019-523049 A | | 8/2019 |
| JP | 2019-523664 A | | 8/2019 |
| JP | 2019-532693 A | | 11/2019 |
| WO | WO-03088143 A2 | * | 10/2003 |
| WO | 2014/025305 A1 | | 2/2014 |
| WO | 2016/066287 A1 | | 5/2016 |
| WO | 2017/185170 A1 | | 11/2017 |
| WO | 2018/223925 A1 | | 12/2018 |

OTHER PUBLICATIONS

Google Translate Machine Translation of IDS (Oct. 25, 2021) cited Leistungssteuerung chirurgischer Instrumente in der Kopf-Chirurgie to Krill Koulechov, translated Mar. 2, 2024, 229 pages. (Year: 2024).*

International Search Report and Written Opinion issued on Aug. 24, 2020 in corresponding International Application No. PCT/EP2020/061522; 18 pages.

Kirill Koulechov, "Leistungssteuerung chirurgischer Instrumente in der Kopf-Chirurgie", Apr. 26, 2006, 156 pages Retrieved from the Internet: URL:https://mediatum.ub.tum.de/doc/601976/601976.pdf.

Hartwig Atze et al., "Quantitative Measurements of Soft Tissue Structures using Image-Features in Navigated Endoscopy", 2016 IEEE 5th Global Conference on Consumer Electronics, IEEE, Oct. 11, 2016; pp. 1-5.

Office Action issued by the U.S. Patent and Trademark Office in U.S. Appl. No. 18/347,837, dated Mar. 6, 2024.

Office Action issued in corresponding Japanese Application No. 2021-563645, dated Oct. 31, 2023, 4 pages, English translation.

* cited by examiner

METHOD AND SYSTEM FOR COMPUTER GUIDED SURGERY

FIELD OF INVENTION

The present invention relates to computer guided surgery. This field comprises a set of computer and/or physical systems designed to assist the surgeon in planning and/or performing a surgical intervention. It includes the following three families of systems: navigation systems, robotic systems and augmented and/or mixed reality guidance systems.

The main elements of current computer guided surgery systems are the following.

First, the creation of a digital model of the patient: either from patient-specific preoperative data obtained by medical imaging (CT scan, MRI, X-rays, etc.) or generated during the surgery by computer processing that combines generic databases (e.g. anatomical atlases, statistical shape models) and the acquisition of intraoperative images (fluoroscopy, ultrasound, etc.) or data of the patient's anatomy obtained using three-dimensional localizers and palpation systems.

Second, the generation of a surgical plan from the computer processing of the digital patient model. This task is performed before the procedure in the case where the patient model is derived from preoperative data, or at the beginning when derived from intraoperative data.

Third, surgical navigation based on a method of matching preoperative data with intraoperative data. Surgical navigation allows the surgeon to visualize the current positioning of the surgical instruments in relation to the patient's anatomy, and to track the progress of the surgery in relation to the surgical planning. In standard navigation systems, this information is displayed on a screen. In mixed reality navigation systems, surgical guidance is displayed by augmented or virtual reality through a helmet or goggles in an augmented or virtual reality manner.

Fourth, a system to assist in the realization of the surgical gesture: patient-specific instrumentation (e.g. customized cutting or milling guides) can be produced from the preoperative planning. Alternatively, visual decision support information is provided to the surgeon. If an electromechanical system assists the surgeon in performing the surgical procedure, it is a robotic system.

This invention belongs to the field of computer guided surgery for the navigation of robotic systems, with unicompartmental and total knee arthroplasty as the main but not exclusive applications.

Computer-assisted robotic arthroplasty uses active or collaborative systems (synergistic systems that combine the skills of the surgeon and the robot to form a performance-enhancing partnership) and passive navigation systems.

BACKGROUND

Two main solutions are generally implemented in the prior art.

The first solution involves the use of markers placed on bone and surgical instruments, combined with an optical tracking system to ensure that real and digital reference points are matched and to know the exact position of bones and surgical instruments in space. An example of this kind of solution is presented in the American patent U.S. Pat. No. 10,136,950 B2 which uses a surgical marker to fit the anatomy of a patient configured to be tracked by a navigation system. To accomplish the accurate planning, tracking and navigation of surgical instruments, tools and/or medical devices during a surgical procedure utilizing surgical navigation, surgeons often couple "tracking arrays" to the surgical markers. These tracking arrays allow the surgeons to track the physical location of these surgical components, as well as the patient's bones during the surgery. By knowing the physical location of the tracking array, software associated with the tracking system can accurately calculate the position of the tracked component relative to a surgical plan image. However, the use of markers that are screwed onto the bone creates a risk of fracture at the anchorage point and lengthens the operating time. Also, the visibility of the markers (Line Of Sight) must be guaranteed during the entire operation, therefore these kinds of solutions are not robust to occlusions, and constrain the positioning of the surgical staff in relation to the surgical field. They multiply the number of steps and tools (markers, probe) and require a mechanical palpation of the anatomical structure to be matched with the digital model. These constraints increase procedure time with tedious work and require the surgeon and the surgical staff to learn how to place the markers and how the operation is carried out. Finally, the associated optical tracking system are cumbersome and expensive.

Furthermore, no purely optical tracking allows for a real-time control loop. To reach this level of performance, mechanical tracking is required.

The second type of solution involves ionizing intraoperative visualization solutions, such as fluoroscopy. During orthopedic and trauma surgery, a fluoroscopy-based navigation system allows the tracking of surgical instruments and the superposition of their contour onto fluoroscopy images in real time. For fluoro-navigation, the instruments used during the surgical intervention are equipped with markers coupled to a localization system.

However, this second type of solution also suffers from the same disadvantages of the first one: lack of robustness to occlusions, constraining the surgical staff positioning with respect to the surgical field, multiplying the number of instruments needed, bringing additional cumbersome equipment to the surgical room (C-arm devices). This second solution further implies the use of ionizing radiation, which is harmful for both the patient and the surrounding medical staff performing the surgery.

SUMMARY

The present invention is a method allowing the alignment of at least one planned surgical action defined in a virtual environment to a physical surgical action in a real environment, more specifically an operating theatre for an orthopedic surgery.

The implementation of this invention relates, for example, to situations where a trajectory, position, displacement or other actions are first determined by means of a digital simulation, for example a surgical planning simulation, in a virtual referential. In order to be usable in a real environment, it is necessary to transpose this trajectory, position, displacement or other actions into a real referential of the patient, on which the actions are to be applied. To do this, multiple transformations must be determined to match the virtual referential to the real referential of the patient.

Preferably, the invention relates to the automated control of a support for a bone's machining tool, in order to comply with surgical planning.

Another example of application of the invention relates to augmented reality, for controlling the position of an image superimposed on the area of vision of an operator, for example a surgeon, either from an augmented vision goggle or from a projector.

The present invention relates to a system for computer guided surgery comprising a transposition of an action, planned in a virtual environment with respect to a virtual referential $R_P$, to a physical action performed with a surgical tool in a real operating theatre environment for orthopedic surgery of a patient, said surgical tool is fixed to a kinematic chain comprising a sensor unit having at least one sensor configured to follow in real time a spatial configuration of the kinematic chain; said system comprising:

a reception module configured to receive at least one 3D image acquired from at least one 3D imaging sensor; said 3D image comprising at least one portion of a target anatomical structure of the patient;

a calculation module configured to:
  calculate a transformation $^CT_P$ between the virtual referential $R_P$ and a target referential $R_C$ and a transformation $^CT_A$ between an acquisition referential of the 3D imaging sensor $R_A$ and the target referential $R_C$ by registration of a digital model of the target with the at least one portion of the target comprised in the 3D image;
  apply the transformation $^CT_P$ so as to register said digital model of the target in the target referential $R_C$ so that each point comprised in the digital model of the target has a known position in the target referential $R_C$;
  calculate a transformation $^CT_O$ between a referential of the surgical tool $R_O$ and the target referential $R_C$;
  apply the transformation $^CT_O$ to the referential of the surgical tool $R_O$ so as to know the position and spatial orientation of the surgical tool in the target referential $R_C$; so as to know the position and spatial orientation of said surgical tool in both the virtual referential $R_P$ and the target referential $R_C$ in order to reproduce the action planned in the virtual referential $R_P$ in the target referential $R_C$.

According to one embodiment, the calculation module is further configured to calculate the transformation $^CT_A$ by:
  defining a region of interest in the 3D image comprising said target;
  registering said region of interest comprising the target to the digital model of the target so as to determine $^CT_A$.

According to one embodiment, defining a region of interest comprises an automated detection of said region of interest by means of a segmentation algorithm.

According to one embodiment, the kinematic chain comprises at least one mechanical reference rigidly fixed to the target anatomical structure and the at least one 3D image comprises at least one portion of the mechanical reference; the calculation module is further configured to:
  calculate a transformation $^OT_M$ between the referential of the surgical tool $R_O$ and the referential of the mechanical reference $R_M$ using the data obtained from the sensor unit comprised in the kinematic chain;
  calculate a transformation $^MT_A$ between the referential of the mechanical reference $R_M$ and the acquisition referential $R_A$ by matching a digital model of the mechanical reference with the at least one portion of the mechanical reference comprised in the 3D image;
  so that the $^CT_O$ transformation is obtained from the combination of the transformations $^OT_M$, $^MT_A$ and $^CT_A$ between the acquisition referential $R_A$, the mechanical reference referential $R_M$ and the target referential $R_C$.

According to one embodiment wherein the target anatomical structure is fixed on the at least one mechanical reference, the system further comprises a correction module configured to track the movements of the target with respect to the surgical tool using the sensor unit of the kinematic chain and, so that whenever a deviation in the position and/or spatial orientation of the target is detected, the transposition of the planned actions from the virtual environment to the real environment is corrected for said deviation. This embodiment advantageously allows to avoid needing a visual tracking or a new registration procedure when the patient moves.

According to one embodiment, the at least one 3D imaging sensor is fixed to the kinematic chain, the calculation module is further configured to calculate a transformation $^AT_O$ between the referential of the surgical tool $R_O$ and the acquisition referential of the 3D imaging sensor $R_A$ from data obtained from the sensor unit of the kinematic chain so that the $^CT_O$ transformation is obtained from the combination of the transformation $^AT_O$ and the transformation $^CT_A$ between the acquisition referential $R_A$ and the target referential $R_C$.

According to one embodiment, the acquisition of the 3D image received by the reception module is carried out using at least two sensors and a projector to carry out an acquisition by stereovision or structured light.

According to one embodiment, the 3D imaging sensor fixed on the kinematic chain moves along a known trajectory and multiple 3D images are acquired along the trajectory, the calculation module is further configured to jointly process multiple 3D images acquired along the trajectory so as to use multiple 3D images for the registration with the digital model of the target.

According to one embodiment, the reception module is further configured to receive a thermal image, an ultrasound image, a multispectral image, an image on a microscopic scale and/or a monocular color image.

According to one embodiment when the 3D imaging sensor is fixed to the kinematic chain, the system further comprises a correction module configured to track the movements of the target with respect to the surgical tool using the 3D imaging sensor and a visual tracking algorithm, so that whenever so that whenever a deviation in the position and/or spatial orientation of the target is detected, the transposition of the planned actions from the virtual environment to the real environment is corrected for said deviation.

The present invention relates to a method for computer guided surgery comprising a transposition of an action, planned in a virtual environment with respect to a virtual referential $R_P$, to a physical action performed with a surgical tool in a real operating theatre environment for orthopedic surgery of a patient, said surgical tool is fixed to a kinematic chain comprising a sensor unit having at least one sensor configured to follow in real time a spatial configuration of the kinematic chain; said method comprising the following steps:

receiving of at least one 3D image acquired from at least one 3D imaging sensor; said 3D image comprising at least one portion of a target anatomical structure of the patient;

calculating a transformation $^CT_P$ between the virtual referential $R_P$ and a target referential $R_C$ and a transformation $^CT_A$ between an acquisition referential of the 3D imaging sensor $R_A$ and the target referential $R_C$ by a registration of a digital model of the target with the at least one portion of the target comprised in the 3D image;

applying the transformation $^CT_P$ so as to register said digital model of the target in the target referential $R_C$ so that each point comprised in the digital model of the target has a known position in the target referential $R_C$;

calculating a transformation $^CT_O$ between a referential of the surgical tool $R_O$ and the target referential $R_C$;

applying the transformation $^CT_O$ to the referential of the surgical tool $R_O$ so as to know the position and spatial orientation of the surgical tool in the target referential $R_C$;

so as to know the position and spatial orientation of said surgical tool in both the virtual referential $R_P$ and the target referential $R_C$ in order to reproduce the action planned in the virtual referential $R_P$ in the target referential $R_C$.

According to one embodiment, the calculation of transformation $^CT_A$ comprises the following steps:

defining a region of interest in the 3D image comprising said target;

registering said region of interest comprising the target to the digital model of the target so as to determine $^CT_A$.

According to one embodiment, the step of defining a region of interest comprises an automated detection of said region of interest by means of a segmentation algorithm.

According to one embodiment, the at least one 3D imaging sensor is fixed to the kinematic chain the method further comprises the steps of calculating a transformation $^AT_O$ between the referential of the surgical tool $R_O$ and the acquisition referential of the 3D imaging sensor $R_A$ from data obtained from the sensor unit of the kinematic chain so that the $^CT_O$ transformation is obtained from the combination of the transformation $^AT_O$ and the transformation $^CT_A$ between the acquisition referential $R_A$ and the target referential $R_C$.

According to one embodiment, the kinematic chain comprises at least one mechanical reference rigidly fixed to the target anatomical structure and the at least one 3D image comprises at least one portion of the mechanical reference; the method further comprises the steps of:

calculating a transformation $^OT_M$ between the referential of the surgical tool $R_O$ and the referential of the mechanical reference $R_M$ using the data obtained from the sensor unit comprised in the kinematic chain;

calculating a transformation $^MT_A$ between the referential of the mechanical reference $R_M$ and the acquisition referential $R_A$ by matching a digital model of the mechanical reference with the at least one portion of the mechanical reference comprised in the 3D image;

so that the $^CT_O$ transformation is obtained from the combination of the transformations $^OT_M$, $^MT_A$ and $^CT_A$ between the acquisition referential $R_A$, the mechanical reference referential $R_M$ and the target referential $R_C$.

According to one embodiment wherein the mechanical reference is rigidly fixed to the target anatomical structure, the movements of the target with respect to said surgical tool are tracked by the sensor unit of the kinematic chain, so that whenever a deviation in the position and/or spatial orientation of the target is detected, the transposition of the planned actions from the virtual environment to the real environment is corrected for said deviation.

According to one embodiment, said kinematic chain consists of a deformable structure comprising multiple rigid elements connected by joints.

According to one embodiment, said kinematic chain further comprises sensors for measuring the forces applied to its elements.

According to one embodiment, the acquisition of the 3D image received by the reception module is carried out using at least two sensors and a projector to carry out an acquisition by stereovision or structured light.

According to one embodiment, the 3D imaging sensor fixed on the kinematic chain moves along a known trajectory and multiple 3D images are acquired along the trajectory, the method further comprises a step of jointly processing multiple 3D images acquired along the trajectory so as to use multiple 3D images for the registration with the digital model of the target.

According to one embodiment, the method further comprises receiving a thermal image, an ultrasound image, a multispectral image, an image on a microscopic scale and/or a monocular color image.

According to one embodiment where the 3D imaging sensor is fixed on the kinematic chain, the movements of the target with respect to said surgical tool are tracked by the 3D imaging sensor and a visual tracking algorithm, so that whenever a deviation in the position and/or spatial orientation of the target is detected, the transposition of the planned actions from the virtual environment to the real environment is corrected for said deviation.

According to one embodiment, the three-dimensional digital model of the target is generated from computed tomography images or MRI images.

According to one embodiment, the three-dimensional digital model of the target is generated using 2D X-ray radiographies comprising the target, a statistical shape model of the target and/or the 3D image acquired intraoperatively by the 3D imaging sensor.

According to one embodiment, the three-dimensional digital model of the target is digitally modified to simulate measurement noise or the presence of cartilage, said modifications being calculated from training data or biomechanical simulation data.

According to one embodiment, the action of matching a digital model of the target with the at least one portion of the target comprised in the 3D image is a non-rigid transformation.

The present invention further relates to a computer program product comprising instructions which, when the program is executed by a computer, cause the computer to carry out the steps of the method according to any one of the embodiments described herein.

The present invention also relates to a computer-readable storage medium comprising instructions which, when executed by a computer, cause the computer to carry out the steps of the method according to any one of the embodiments described herein.

As described above, one embodiment of the present invention relates to a method for computer guided surgery using a kinematic chain comprising at least one mechanical reference rigidly fixed to the target anatomical structure. The following paragraphs relates to this specific embodiment.

The method implements a mechanical reference kinematically linked through the kinematic chain with the surgical tool: during the entire operation, the position and orientation of the surgical tool in relation to the mechanical reference are known thanks to position and/or displacement sensors of the components of the kinematic chain. On the other hand, the mechanical reference is rigidly linked to the bone element to be machined (i.e. target). During the operation, the invention uses depth data (also called 3D images) to perform a registration of the bone element with planning data obtained preoperatively or intraoperatively (at the beginning of the operation, after soft tissues incision but before bone resections), said planning data comprising the digital model of the target and the planned surgical action to be performed during the orthopedic surgery. In this way, the position and orientation of the mechanical reference with respect to the target is determined. The registration process and the knowledge of the kinematic chain's geometry make it possible to determine the trajectory of the surgical tool in the reference frame of the target. The position and orientation of the surgical tool relative to the bone element is known at all times and its path can be corrected in the event, for instance, of patient movement, in order to comply with the previously established surgical planning.

The present invention overcomes the disadvantages of the prior art in that it does not require ionizing imaging or multiple optical markers to enable a surgical tool holder to be controlled in order to perform the actions comprised in the surgical planning Both being potentially harmful and time consuming, the present invention presents a direct health benefit both for medical teams and patients. It also offers advantages in terms of procedure length and ease of use for the surgeon.

The present invention relates to a method comprising the following steps.

A first step of acquisition of at least one 3D image from a 3D image sensor(s) of a scene including:
  at least one portion of a target (i.e. the bone element to be machined);
  at least one portion of the mechanical reference kinematically linked to said tool.

A second step of mapping said 3D image to a digital model of the target by applying image processing algorithms so as to determine the transformation $^{C}T_{A}$ which defines the position and spatial orientation of the acquisition referential $R_A$ with respect to the referential of the target $R_C$.

A third step of mapping said 3D image to a digital model of the mechanical reference, making it possible to determine the transformation $^{M}T_{A}$ which defines the position and orientation of the acquisition referential of the 3D image sensor $R_A$ with respect to the referential of the mechanical reference $R_M$.

A fourth step of calculating the transformation matrix between the target referential $R_C$ and the mechanical reference referential $R_M$ using the $^{C}T_{A}$ and $^{M}T_{A}$ transformation matrices.

A fifth step of transposition of the initial planning into the target referential $R_C$.

In parallel, the method comprises steps of real-time acquisition of the positions, spatial orientation and/or displacements of the elements of the kinematic chain linking said mechanical reference to said surgical tool during said physical action using the surgical tool.

Advantageously, the present method does not rely on real-time optical monitoring of the scene. It therefore avoids the problems associated with standard surgical navigation systems such as the multiplicity of markers and the loss of tracking in the event of occlusion of the operating area. Indeed, once the planning data are known in the target referential $R_C$, the sensors of the kinematic chain provide knowledge of the position and orientation of the surgical tool in relation to the target to be calculated at any time.

According to a variant, the said second and third mapping steps are replaced by the following steps.

A region of interest extraction step consisting of extracting a first region of interest corresponding to said target and a second region of interest corresponding to said mechanical reference to determine:
  a first subset of said 3D digital image associated with said target;
  a second subset of said 3D digital image associated with said mechanical reference.

The extraction of the regions of interest can be performed automatically through segmentation algorithms.

A step of mapping said first subset associated with said target to the digital model of said target to determine the transformation $^{C}T_{A}$.

A step of mapping said subset associated with said mechanical reference to the digital model of said mechanical reference to determine the transformation $^{M}T_{A}$.

According to variations of the embodiment, taken individually or in a technically realistic combination, the invention also relates to the following additional features:
  the kinematic chain consists of a rigid deformable structure comprising sensors measuring the relative positions of its constituents;
  said first step of acquiring a 3D image is carried out by textured 3D image acquisition using at least two cameras and a projector to carry out an acquisition by stereovision;
  said first step of acquiring a 3D image is carried out by textured 3D image acquisition using at least two sensors and a projector to carry out an acquisition by structured light;
  said first acquisition step further comprises acquisition of an RGB-D image;
  said first acquisition step further comprises acquisition of a thermal image;
  said first acquisition step further includes ultrasonic image acquisition;
  said first acquisition step further comprises acquisition of a multispectral image;
  said first acquisition step further comprises an acquisition of an image on a microscopic scale;
  said first acquisition step further includes acquisition of a monocular color image;
  the movements of said surgical tool with respect to the target are tracked by means of position and/or displacement sensors of the elements of the kinematic chain between the target and said surgical tool, making it possible to correct the transposition of the actions planned in a virtual environment to the real environment;
  said three-dimensional digital model of the target has been generated from scanner or MRI images;
  said three-dimensional digital model of the target has been digitally modified to simulate measurement noise or the presence of cartilage, said modifications being calculated from training data or biomechanical simulation data;

Advantageously, said digital resetting processing of the second step making possible to determine the transformation $^{C}T_{A}$ which defines the position and orientation of the acquisition referential $R_A$ with respect to the target referential $R_C$ is non-rigid.

In the present invention, the following terms have the following meanings:
  "3D sensor" or "3D camera" or "Depth Camera" or "3D scanner" refers to a 3D sensor is a system for acquiring topological data of a real scene in 3 dimensions. These topological data are recorded in the form of a point cloud, and/or a depth map.
  Multiple acquisition technics allow to obtain these topological data for example:
    technics based on the measure of waves propagation time such as ultrasound or light (LIDAR, Time-of-Flight);

stereoscopic camera or sensor, which is a type of camera with two or more lenses with a separate image sensor or film frame for each lens. This allows the camera to simulate human binocular vision, and therefore gives it the ability to capture three-dimensional images;

technics based on light deformation, such as structured-light 3D scanners which project a pattern of light on an object and look at the deformation of the pattern on the object. The advantage of structured-light 3D scanners is speed and precision. Instead of scanning one point at a time, structured light scanners scan multiple points or the entire field of view at once. Scanning an entire field of view in a fraction of a second reduces or eliminates the problem of distortion from motion;

technics based on laser scanning for sample or scan a surface using laser technology, such as hand-held laser or time-of-flight 3D laser scanner;

These terms may as well refer to an RGB-D, color, multispectral, or a thermal camera.

"Referential" refers to a coordinate system that uses one or more numbers, or coordinates, to uniquely determine the position of the points or other geometric elements on a manifold such as Euclidean space.

"Tracking", in computer vision, refers to the action of following the position and spatial orientation of an object between successive images of a stream. Marker-based tracking relies on the use of a localization device associated to a marker attached to the object of interest. Marker-less tracking relies on extracting visual features from the object of interest itself and matching them on a frame-to-frame basis.

"Registration" or "Matching" or "Pose estimation" refers to the process of transforming different sets of data into one coordinate system.

"Tridimensional digital model" refers to a three-dimensional digital (or virtual) model being a virtual object in 3 dimensions. The position and orientation of the model is known in the associated digital referential.

"Planning", in the context of surgery, refers to a list of actions to be performed during the different surgical phases. This surgical planning may be obtained by means of a simulation program carried out before the operation which uses a 3-dimensional digital model of the bone(s) of the patient that are the target of the surgery. In the case of a knee arthroplasty operation, for example, pre-operative planning will consist of defining each of the machining planes and drilling axes in relation to a three-dimensional model of the femur and tibia.

"Pre-operative data" refers to images (or slices) of the patient obtained by medical imaging (CT, MRI, PET, etc.). The three-dimensional model of the patient is obtained by a segmentation treatment of each image, followed by an interpolation between the images.

"Intraoperative data" refers to data acquired during the operation. This may include medical imaging (fluoroscopy, ultrasound, etc.), three-dimensional data, color and temperature information, information from proprioceptive sensors, force feedback with respect to a surgical tool, etc.

"Machining" refers to the mechanical process of cutting or other methods for removing material. The purpose of machining is to modify the dimensions, precision, geometry and surface state of all the surfaces of the finished element, in order to move from a raw original state to a final state in accordance with a predefined model.

DETAILED DESCRIPTION

Figure 1A:
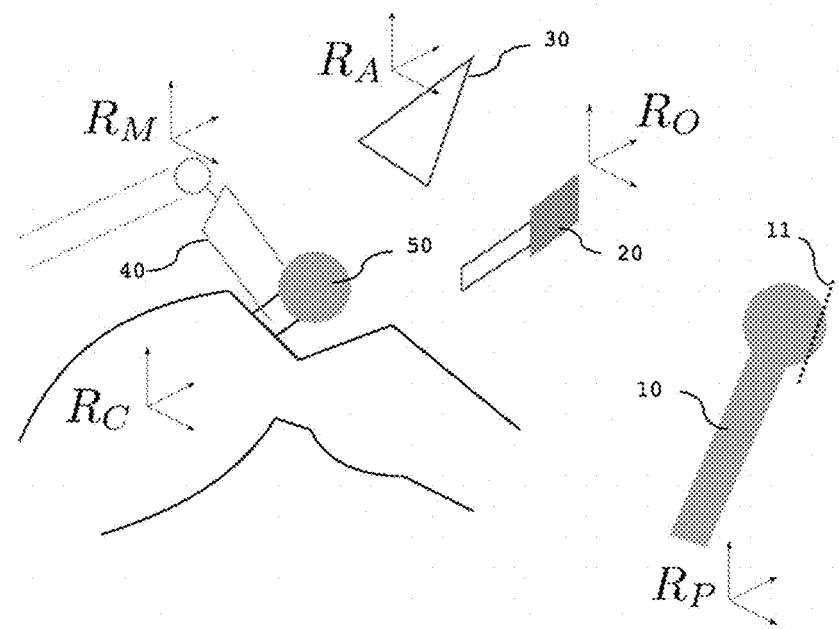
FIGS. 1A and 1B show a schematic view of the different referential systems defined in the present invention according to the embodiment where the kinematic chain comprises at least one mechanical reference.

The following detailed description will be better understood when read in conjunction with the drawings. For the purpose of illustrating, the steps implemented by the system and the method are shown in the preferred embodiments. It should be understood, however that the present invention is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings.

While various embodiments have been described and illustrated, the detailed description is not to be construed as being limited hereto. Various modifications can be made to the embodiments by those skilled in the art without departing from the true spirit and scope of the disclosure as defined by the claims.

The purpose of the present invention is to match, in an uninterrupted and real-time manner, the pre-operative planning data with the actual procedure taking place in the surgical theater.

The pre-operative surgical planning comprises a 3D digital model of at least a part of the patient, notably comprising the target bone element, and an ordered set of geometrical equations characterizing the machining actions on the patient's target bone elements. In a preferred embodiment, the pre-operative surgical planning comprises the machining plan corresponding to each surgical action. With the term pre-operative surgical planning it is understood that the surgical actions of the surgical planning have been defined using planning data obtained before the surgery (pre-operatively) or intraoperatively during the first phase of the surgery when the target bone element is exposed but before the beginning of the surgical action on the target bone.

The digital model of the target may be generated from medical images acquired prior to the operation. It can be modified to take into account elements that are not visible in the medical images, for example cartilage that is not visible in CT scan images. In this case, the modifications are generated from training data or biomechanical simulation data. The digital model can also be generated from statistical models or abacuses and patient data associated or not with the preoperative medical images. In addition, the digital model can be adapted taking into account data acquired during the operation.

Planning data for the determination of the pre-operative surgical planning are acquired in a place, time and with a position of the patient with respect to the imaging means that can be completely independent from the ones of the surgery. However, the digital data of the digital planning model must be brought closer to physical reality in order to allow a control of the movements of the real machining tool as function the digital planning data.

For the rest of the description, the following references will be considered:

the planning or virtual referential $R_P$ of digital planning images and surgical actions of the surgical planning stored in a computer's memory. The bone element to be machined in the digital model of the target, in the described example a femur 10, has a known position and spatial orientation in this virtual referential $R_P$. The surgical planning data and surgical actions (e.g. the position of the cutting planes 11 or the drilling axes) are known in the same referential $R_P$;

the target referential $R_C$ corresponds to the physical coordinate system of the bone element to be machined (i.e. target), in this case the surface of the femoral head;

the surgical tool referential $R_O$ corresponds to the physical coordinate system of the surgical tool 20;

the acquisition referential $R_A$ corresponds to the 3D imaging sensor 30 coordinate system in which the data acquired during the operation are represented the mechanical referential $R_M$ corresponds to the physical coordinate system of the mechanical reference 40 kinematically linked to the surgical tool 20 through the element of the kinematic chain. The position and spatial orientation of the surgical tool 20 relative to the mechanical reference 40 are known by the sensors of the kinematic chain providing signals representative of the angular and/or linear displacements of the surgical tool 20 with respect to the mechanical reference 40.

Figure 9:
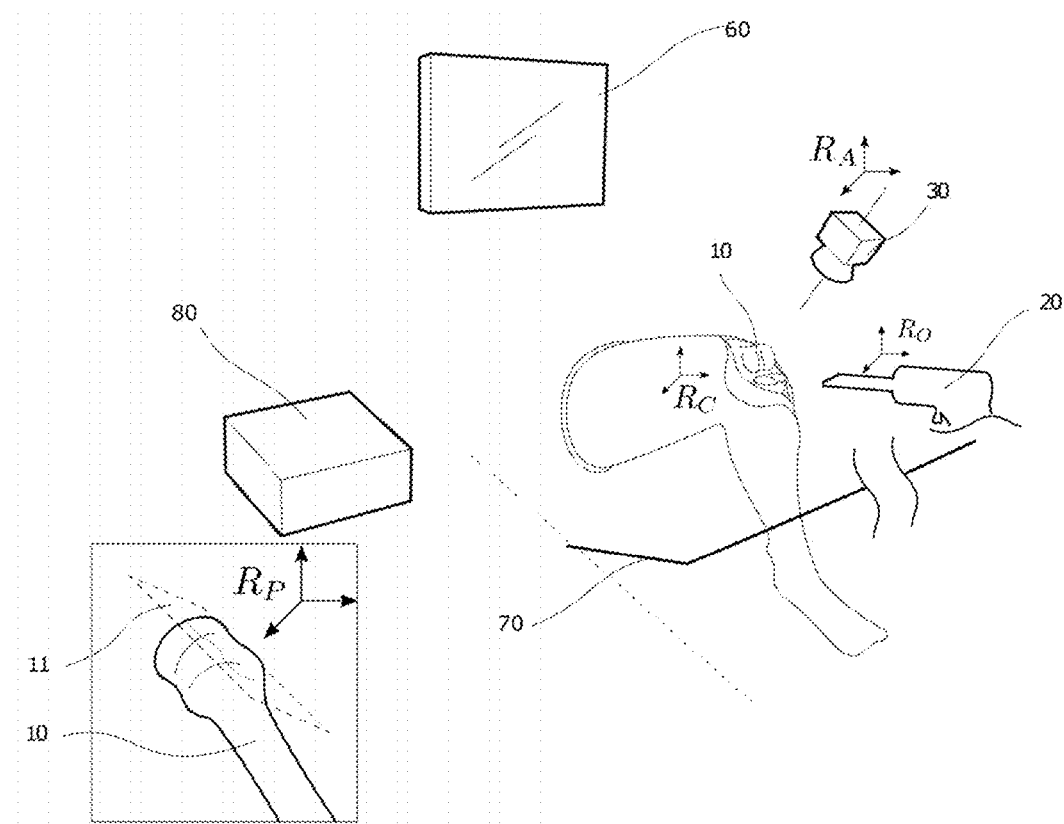
FIG. 9 shows an example of the system of the present invention and the kinematic chain comprising the surgical tool at one end, the 3D imaging sensor having a known position with respect to the patient.

The positioning of the bone target 10, the kinematic chain 70, the surgical tool 20, the 3D imaging sensor 30 and their respective referential are represented in FIG. 9.

The present method aims to accurately guide a surgical tool 20 movably fixed to a kinematic chain 70. Said surgical tool 20 may be for example a machining tool.

In the present invention the term kinematic chain refers to an ensemble of rigid elements connected by joints to constrain or provide motion in a desired way.

According to one embodiment, said kinematic chain consists of a deformable structure comprising multiple rigid elements connected by joints.

According to the present invention, the kinematic chain comprises a sensor unit having at least one sensor configured to follow in real time a spatial configuration of said kinematic chain.

The sensors of the sensor unit may be encoders or inertial units comprising accelerometer and/or gyroscopes.

According to one embodiment, said kinematic chain further comprises sensors for measuring the forces applied to its elements.

In one embodiment, the first step of the present method comprises receiving at least one 3D image acquired from at least one 3D imaging sensor 30 wherein the 3D image is acquired so as to comprise at least one portion of a target anatomical structure 10 of the patient.

The 3D image obtained from the 3D imaging sensor 30 of the present invention comprises information of the distance between each point of the scene acquired in the image and the 3D imaging sensor 30. Therefore, the raw 3D image obtained by the 3D imaging sensor 30 is a so called a depth map, or depth image that may be presented under the form of a bidimensional array representing a grey level image or a RGB image, wherein the size of the array depends on the camera type and sensor dimensions.

According to one embodiment, the acquisition of the 3D image is carried out using at least two cameras and a projector to carry out an acquisition by stereovision or structured light.

The use of a 3D imaging sensor advantageously allows to obtain information on the morphology of the bone surface in an easy and fast way since one image allows to capture all the surgical field, without coming into contact with the patient (as for palpation techniques).

According to one embodiment, the method further comprises a pre-processing step implementing noise reduction algorithms.

According to one embodiment, the at least one 3D imaging sensor 30 has a fixed position with respect to the target 10 in the surgical theatre. In this embodiment, the 3D imaging sensor 30 is independent from the kinematic chain (i.e. the 3D imaging sensor is not fixed to the kinematic chain). In one example, the 3D imaging sensor 30 is fixed on a wall of the surgical theatre or is positioned on a tripod or fixed by means of an articulated arm. In case the 3D imaging sensor 30 is displaced so as to capture multiple 3D images, an inertial measurement unit (IMU) fixed to the 3D imaging sensor 30 can measure its relative movement and determine the motion trajectory.

Figure 12:
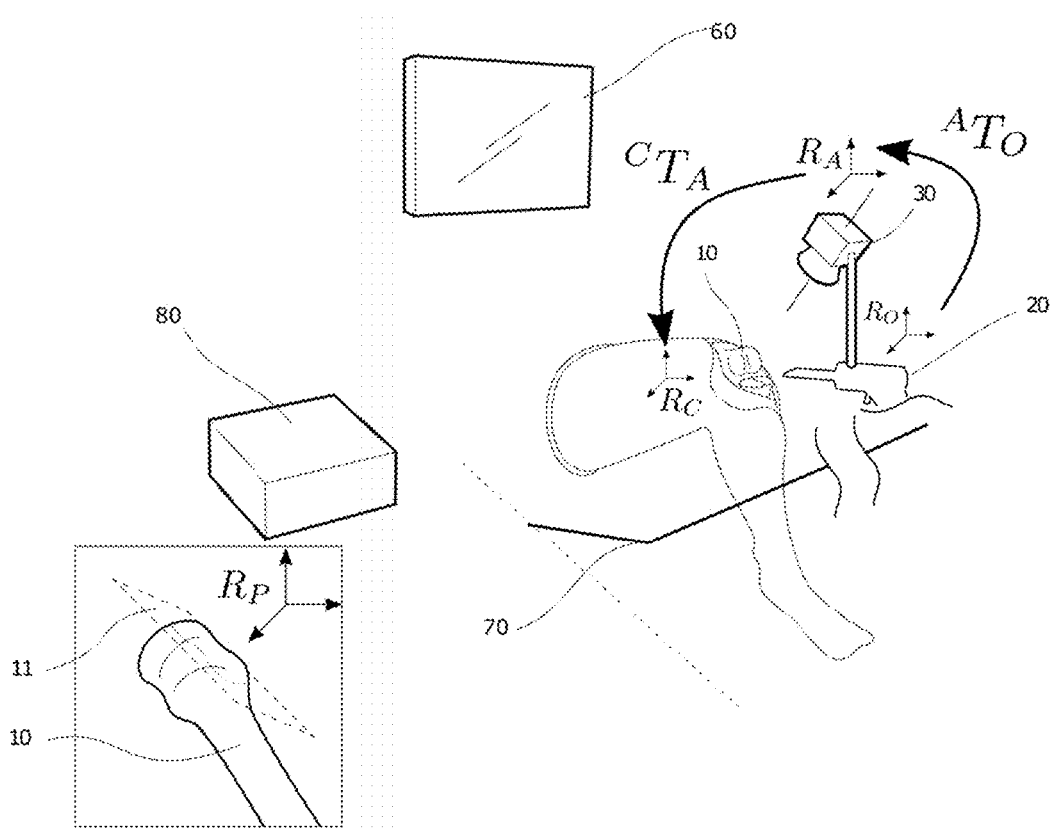
FIG. 12 is a schematic representation the embodiment where the at least one 3D imaging sensor is fixed onto the kinematic chain. In this figure are as well illustrated the transformation $^AT_O$ between the referential of the surgical tool $R_O$ and the acquisition referential of the 3D imaging sensor $R_A$ and the transformation $^CT_A$ between the acquisition referential $R_A$ and the target referential $R_C$, which are used to calculate the transformation $^CT_O$.

According to an alternative embodiment, the at least one 3D imaging sensor 30 is fixed to the kinematic chain as illustrated in FIG. 12. This advantageously allows to have access at all times during the surgery to the relative position of the surgical tool 20 with respect to the 3D imaging sensor 30.

When the at least one 3D imaging sensor 30 is fixed to the kinematic chain 70 then the 3D imaging sensor moves along a known trajectory, the 3D imaging sensor 30 may acquire multiple 3D images along this trajectory.

According to one embodiment, the first step further comprises receiving a thermal image, an ultrasound image, a multispectral image, an image on a microscopic scale and/or a color image.

According to one embodiment, the method comprises retrieving from a computer readable storage medium, a server or the like a digital model of the target bone to be treated during the surgery using the surgical tool 20. Said digital model is a three-dimensional virtual representation of the target bone 10.

In one embodiment, the three-dimensional digital model of the target is generated using imaging data acquired using computed tomography or MRI systems. Other imaging techniques may be as well used such as X-rays, fluoroscopy, ultrasound or other imaging means. In this case, the three-dimensional digital model is obtained previous to the surgery.

In one embodiment, the three-dimensional digital model of the target is generated using 2D X-ray radiographies comprising the target, a statistical shape model of the target and/or the 3D image acquired intraoperatively by the 3D imaging sensor 30.

This embodiment advantageously allows to generate a three-dimensional model even when the 3D imaging data (i.e. computed tomography or MRI) are not available.

In one embodiment, the three-dimensional digital model of the target is modified to simulate measurement noise or the presence of cartilage. Said modifications may be calculated from training data or biomechanical simulation data.

Figure 2:
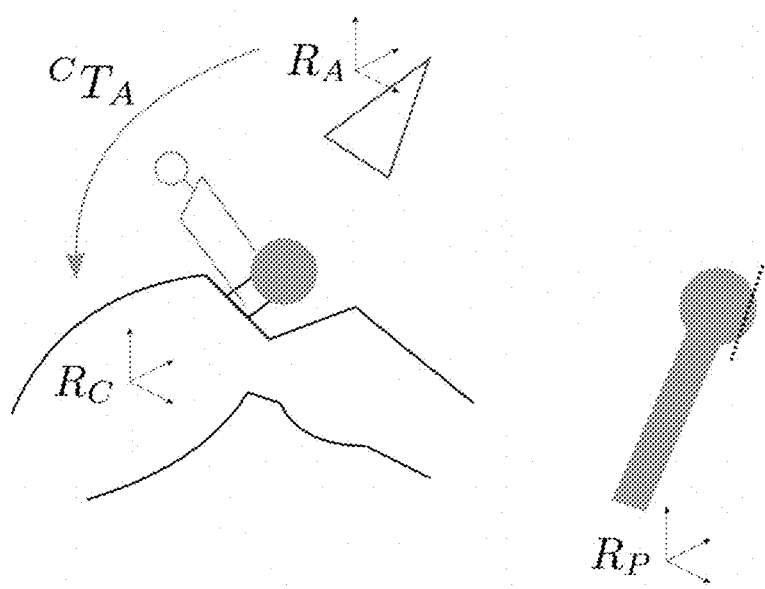
FIG. 2 shows a schematic view of the step of the process where the target referential $R_C$ and the virtual referential $R_P$ are aligned to determine the $^CT_A$ transformation that defines the position and orientation of the acquisition referential $R_A$ with respect to $R_C$. $^CT_A$ is a homogenous transformation matrix composed of a $^CR_A$ rotation matrix and a $^CT_A$ translation vector. It defines the position of target referential $R_C$ with respect to acquisition referential $R_A$.
Figure 10:
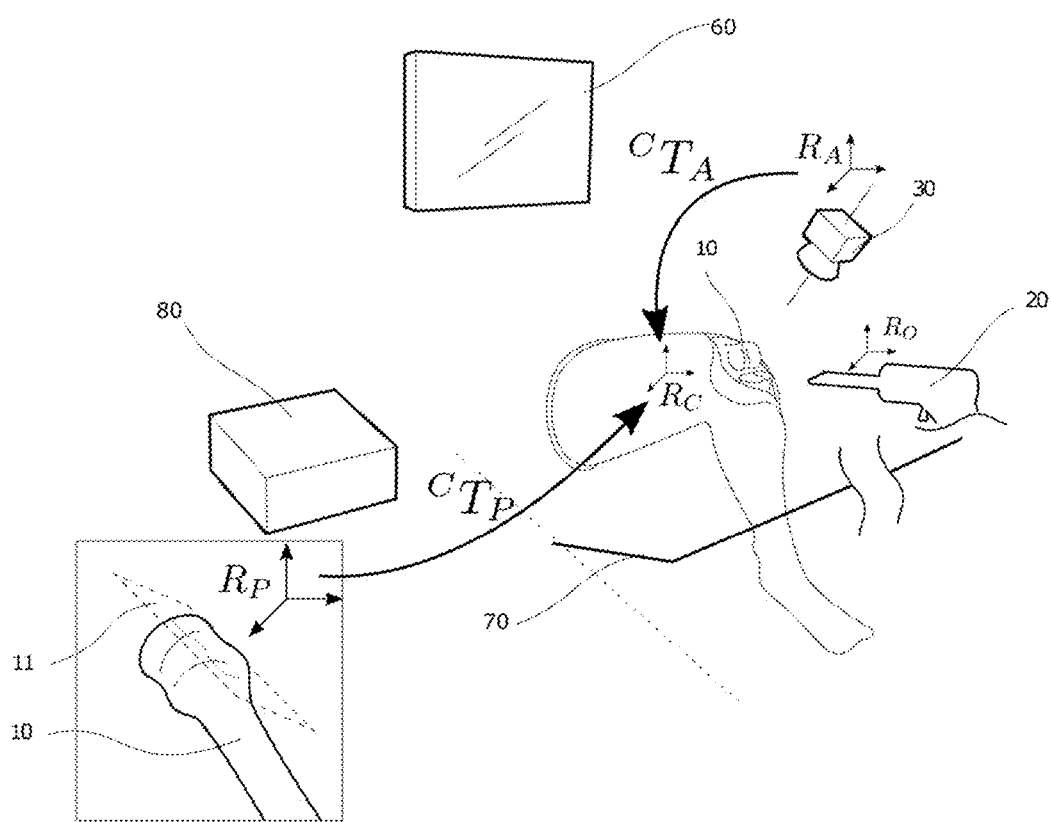
FIG. 10 schematically represent the step of calculating a transformation $^CT_P$ between the virtual referential $R_P$ and a target referential $R_C$ and a transformation $^CT_A$ between an acquisition referential of the 3D imaging sensor $R_A$ and the target referential $R_C$.

According to one embodiment illustrated in FIGS. 2 and 10, a further step of the method comprises calculating a transformation $^{C}T_P$ between the virtual referential $R_P$ and a target referential $R_C$ and a transformation $^{C}T_A$ between an acquisition referential of the 3D imaging sensor $R_A$ and the target referential $R_C$ by a registration of the digital model of the target with the at least one portion of the target 10 comprised in the 3D image.

3D registration consisting in finding the transformation between two 3D models of the same object such that their overlapping areas match as well as possible. This can be performed by an algorithm that iteratively aligns the two models by alternating a matching step associating each point of the intraoperative image to its nearest neighbor in the preoperative model, and a transformation estimation step which transforms the intraoperative model as to best fit the estimated matches. This process is repeated until the distance between each point of the intraoperative and preoperative model is minimized, below a threshold value.

This step advantageously allows to know the transformation that aligns the virtual referential $R_P$ to the target referential $R_C$ in the surgical theatre. Furthermore, the use of a digital model of the bone and its registration to at least one 3D image of target in the surgical field allows to know the transformation between the between the virtual referential $R_P$ and a target referential $R_C$ independently from any external marker attached to the patient.

In one embodiment, the registration of the digital model of the target with the at least one portion of the target comprised in the 3D image is obtained from a rigid transformation.

Alternatively, the registration of the digital model of the target with the at least one portion of the target comprised in the 3D image may be a non-rigid transformation.

Advantageously, this embodiment allows to adapt the shape of the digital model of the target obtained from pre-acquired images to the 3D image acquired during the surgery.

According to one embodiment, the step of calculating the transformation $^{C}T_A$ comprises a first step of defining a region of interest in the 3D image which comprises at least a portion of the target.

According to one embodiment, the step of defining a region of interest comprises an automated detection of said region of interest by means of a segmentation algorithm.

Alternatively, an operator may provide as input to the method information comprising a manual delineation of the contour of the region of interest of the target.

This region of interest comprising the target is then registered to the digital model of the target so as to determine $^{C}T_A$.

In one embodiment, the method further comprises a step of applying the transformation $^{C}T_P$ so as to register said digital model of the target in the target referential $R_C$ so that each point comprised in the digital model of the target has a known position in the target referential $R_C$. This step advantageously allows to align the virtual referential to which are associate the digital model of the target and the actions of the surgical planning to the target referential $R_C$ in the surgical theatre.

Figure 11:
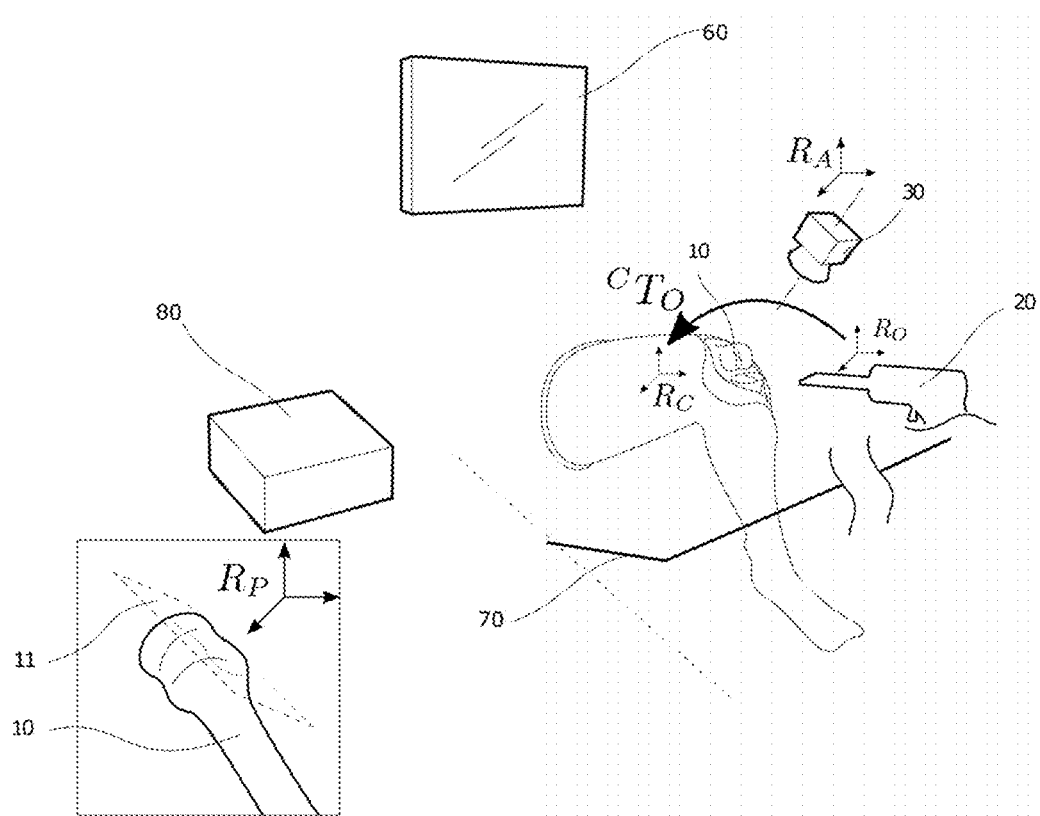
FIG. 11 schematically represent the step of calculating a transformation $^CT_O$ between a referential of the surgical tool $R_O$ and the target referential $R_C$.

In one embodiment illustrated in FIG. 11, the method comprises a step of calculating a transformation $^{C}T_O$ between a referential of the surgical tool $R_O$ and the target referential $R_C$.

The method then may implement a step of applying the transformation $^{C}T_O$ to the referential of the surgical tool $R_O$ so as to know the position and spatial orientation of the surgical tool 20 in the target referential $R_C$. This final step allows to know the position and spatial orientation of said surgical tool 20 in both the virtual referential $R_P$ and the target referential $R_C$ in order to reproduce the action planned in the virtual referential $R_P$ in the target referential $R_C$.

When the position and spatial orientation of said surgical tool 20 in both the virtual referential $R_P$ and the target referential $R_C$ is known, it is possible to make use of the kinematic chain carrying the said surgical tool 20 to guide the performance of the actions planned in the initial surgical planning. However, it may happen that during the performance of these actions the spatial orientation and position of the target is modified, for example by a movement of the target by one of the members of the medical staff. This would result into a mismatch between the virtual referential $R_P$ and the target referential $R_C$ and therefore the surgical tool 20 executing the planned action with reference to the virtual referential $R_P$ would be in a wrong position.

In order to prevent this undesired situation, the movements of the target 10 with respect to said surgical tool 20 may be tracked so that whenever so that whenever a deviation in the position and spatial orientation of the target is detected, the registration of the planned actions from the virtual referential $R_P$ and the target referential $R_C$ is promptly corrected for said deviation.

According to one embodiment where the 3D imaging sensor 30 is fixed to the kinematic chain 70 as shown in FIG. 12, the method is configured to calculate a transformation $^A T_O$ between the referential of the surgical tool $R_O$ and the acquisition referential of the 3D imaging sensor $R_A$ from data obtained from the sensor unit of the kinematic chain and by combining said transformation $^A T_O$ to the transformation $^C T_A$ so as to obtain the $^C T_O$ transformation between the surgical tool $R_O$ and the target referential $R_C$.

In the case where the 3D imaging sensor 30 is fixed to the kinematic chain 70 as shown in FIG. 12, according to one embodiment, the movements of the target 10 with respect to said surgical tool 20 are computed through a visual tracking algorithm using as input the live 3D images captured by the 3D imaging sensor 30 for a continuous pose (i.e. spatial orientation and position) estimation of the target 10 with respect to the 3D imaging sensor 30. The relative motion of the 3D imaging sensor 30 and target 10 is computed by performing a frame-to-frame registration, namely by registering the current 3D image (timestep i) with the previous one (timestep i−1). Since the 3D imaging sensor 30 is mechanically linked to the surgical tool 20, the relative motion estimated from the visual tracking should match the relative motion computed from the sensor units of the kinematic chain 70. If this is not the case, it means that the target 10 has moved and the registration of the planned actions from the virtual referential $R_P$ and the target referential $R_C$ (first three steps of the present method) needs to be performed again to correct the deviations.

According to the alternative embodiment where the kinematic chain 70 is independent from the 3D imaging sensor 30, the kinematic chain 70 comprises at least one mechanical reference 40 rigidly fixed to the target anatomical structure 10. According to this embodiment represented in FIGS. 1A and 1B, the at least one 3D image must comprise at least one portion of the mechanical reference.

Figure 3:
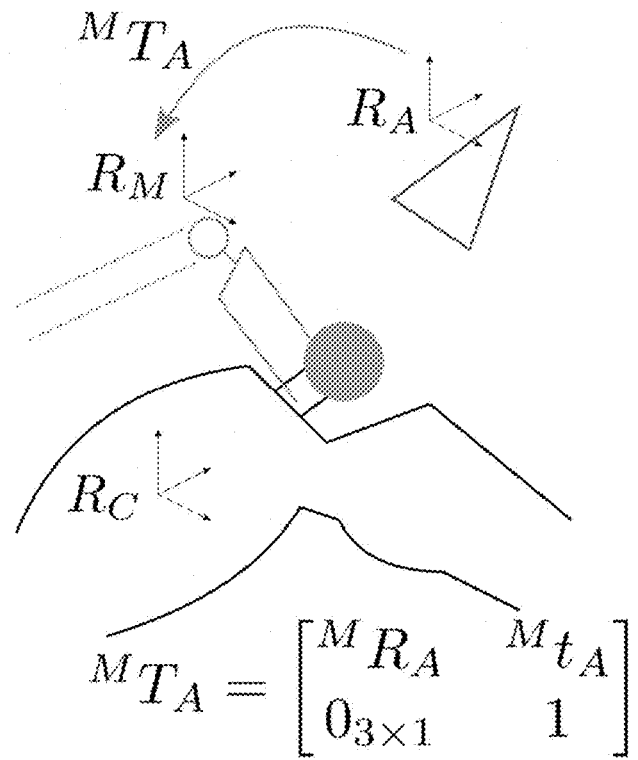
FIG. 3 shows the fourth step according to one embodiment of the invention, where the position and spatial orientation of the mechanical reference referential $R_M$ relative to acquisition referential $R_A$ is determined (transformation matrix $^MT_A$). $^MT_A$ is a homogeneous transformation matrix, composed of a rotation matrix $^MR_A$ and a translation vector $^MT_A$. It defines the position and spatial orientation of mechanical reference referential $R_M$ with respect to acquisition referential $R_A$.

According to this embodiment shown in FIG. 3, the method further comprises the steps of:
- calculating a transformation $^O T_M$ between the referential of the surgical tool $R_O$ and the referential of the mechanical reference $R_M$ using the data obtained from the sensor unit comprised in the kinematic chain 70;
- calculating a transformation $^M T_A$ between the referential of the mechanical reference $R_M$ and the acquisition referential $R_A$ by matching a digital model of the mechanical reference with the at least one portion of the mechanical reference comprised in the at least one 3D image;

so that the $^C T_O$ transformation is obtained from the combination of the transformations $^O T_M$, $^M T_A$ and $^C T_A$ between the acquisition referential $R_A$, the mechanical reference referential $R_M$ and the target referential $R_C$.

Figure 1B:
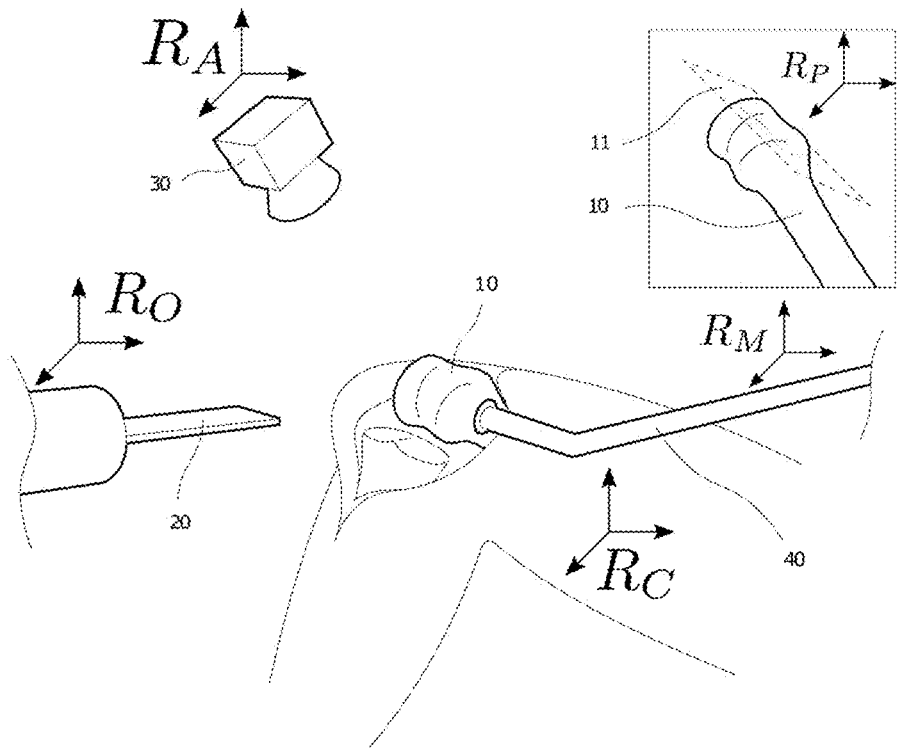
Figure 7:
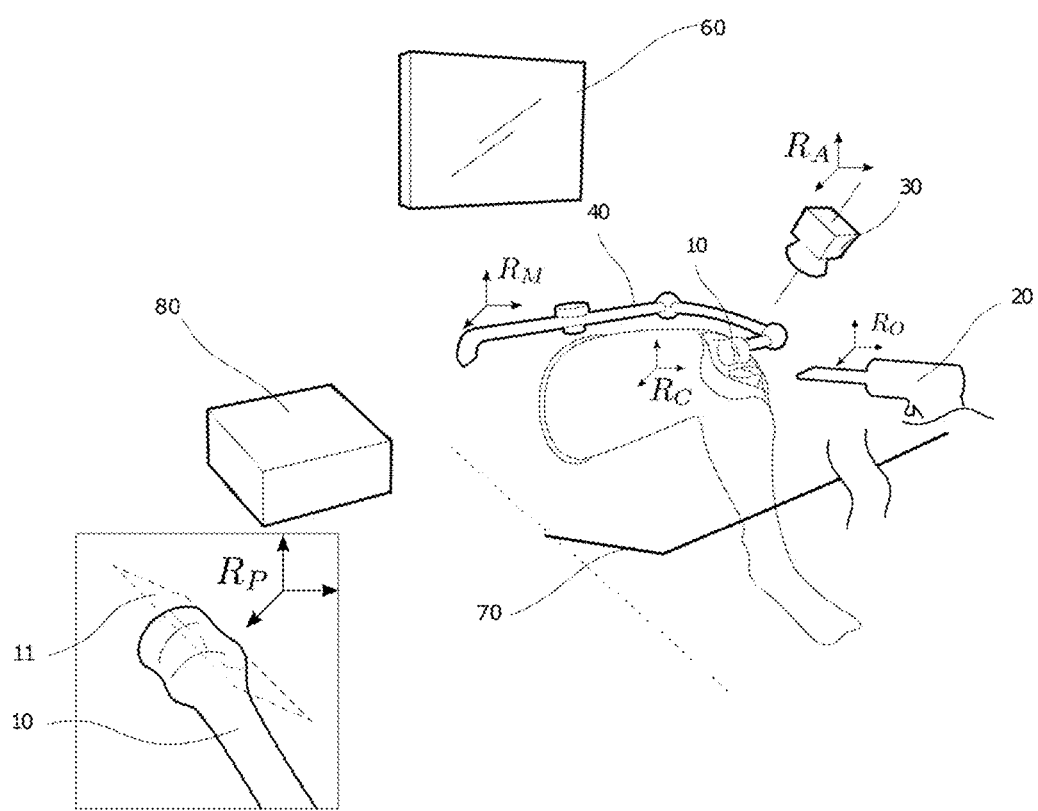

When the mechanical reference 40 is fixed to the target 10 as shown in FIGS. 1, 1B and 7, according to one embodiment, the movements of the target 10 with respect to said surgical tool 20 are tracked by the sensor unit of the kinematic chain 70 so that whenever a deviation in the position and spatial orientation of the target 10 is detected, the registration of the planned actions from the virtual referential $R_P$ and the target referential $R_C$ is promptly corrected for said deviation. Indeed, since the mechanical reference 40 is rigidly fixed to the target anatomical structure 10 while being part of the kinematic chain 70, it is possible to detect all movements of the target 10 with respect to said surgical tool 20 using the information acquired from the sensor unit. This correction may consist in the calculation of a correction transformation $^{Cnew}T_P$ between the new target referential $R_C$ and virtual referential $R_P$ so that each point comprised in the digital model of the target has a known position in the new target referential $R_C$. with mechanical reference The specific embodiments concerning the steps of the method to be implement when a kinematic chain 70 comprising at least one mechanical reference 40 is used, are described in details in the following paragraphs.

As an example, the surgical tool 20 is associated with a tool holder connected to a mechanical reference, such as a gripper or a screw, mechanically fixed to the bone to be machined. The mechanical connection between this tool support and the mechanical reference is provided by a kinematic chain having deformable structure comprising at least two elements, for example an articulated assembly comprising multiples articulated elements and sensor unit having at least one sensor configured provide in real-time a signal as a function of the relative spatial orientation and position of the articulated elements. This sensor unit thus provide digital information making it possible to determine in real time the position in space of the active end of the surgical tool with respect to a fixed point of the element fixed on the bone.

In addition, intraoperative data acquisition and their matching with the digital surgical planning allows the positioning of the mechanical reference fixed on the bone to be known in relation to the bone element surface to be machined. A known trajectory can be transposed into the real world by simulation in a virtual referential, for example to ensure machining tool guidance, control of its movements, or position control in relation to a predetermined position during surgical planning First Step For this purpose, a 3D image is acquired by a 3D imaging sensor 30, for example a camera, whose field of view encompasses part of the operating field in which is comprised at least part of the surface to be machined 10 (for example a femur) and part of the mechanical reference 40. The result of the acquisition can be displayed on a screen 60.

The acquisition can be carried out by a 3D camera, a pair of cameras to acquire images in active stereovision, a 3D scanner or a LIDAR to provide a three-dimensional image of type (x, y, z; a) or a depth map, a point cloud, a designating a parameter such as color or intensity.

3D Image Acquisition of the Operation Scene

A textured 3D digitizing solution uses two or more calibrated cameras and a projector to perform stereovision acquisition and phase-shift structured light acquisition for an accurate 3D reconstruction of the surgical area. The proposed solution integrates a spatio-temporal super-resolution scheme, with non-rigid 3D registration, to correct the 3D information and complete the scanned view.

The structured light is encoded by time multiplexing. Two sinusoidal patterns in phase opposition and a third white pattern are successively projected onto the operative scene. A 2D sampling is first applied for each camera separately to locate the fringe intersection points. A non-dense 3D model of the scene is then estimated for each pair of cameras by stereo matching between the obtained primitives and optical triangulation. The spatial resolution of this model depends on the number of fringes forming the pattern used. A dense 3D model is then obtained by estimating the phase information of the points located inside the fringes, separately for each camera-projector pair used. Conventional phase-shift structured light-based approaches require off-line calibration of the projector with the cameras and a phase unwinding step.

Super-resolution in space and time makes it possible to complete and correct 3D models of the observed scene, since 3D scanning can generate distortions and artifacts caused mainly by occultations, by a variation in the position, or even by light reflection on the acquisition surface. Thus, by using on the one hand the different 3D models provided by all camera pairs and on the other hand the 3D frame calculated at time t−1, a high-resolution 3D model corrected at time t is obtained. The space-time super-resolution is provided by a first 3D matching step followed by a merging and denoising step. A non-rigid 3D matching approach allows to deal with a possible distortion or deformation of the non-rigid observed area. A mesh of the obtained 3D point cloud and a texture plating allow to finalize the textured 3D frame of the instant t.

The result of this first step is the recording in the memory of the computer of a 3D image of the area containing both a visible part of the bone 50 and a visible part of the reference 40, in the form of a point cloud each defined by a luminous intensity, the colors and the coordinates (x, y, z) in the acquisition referential $R_A$.

Additional Imaging Modalities

A particular solution is to acquire additional images of different nature, in the same acquisition referential $R_A$, or in a referential calibrated with $R_A$ to have additional information. Calibration of the additional modality requires the use of a geometric test pattern visible from different angles of view by both the 3D imaging sensor 30 and the additional modality. The resulting image pairs are processed and rescaled to derive the calibration matrix.

The additional image can for example be a thermal image produced by a thermal camera that captures the operating field with an orientation and distance close to that of the 3D imaging sensor 30. This image advantageously makes it easier to distinguish between the patient tissues and the surgical tool.

It can also be an acquisition by a color camera, an ultrasonic probe or a multispectral sensor.

Step 2: Extraction of Areas of Interest

The following processing step consists of exploiting the at least one 3D image recorded during the acquisition step to isolate the portion of the image corresponding to the target 10 (femur), and the portion of the image corresponding to the mechanical reference 40.

To do this, the said 3D digital image of the entire scene, and the image obtained by said additional imagery if present, is processed by algorithms for characterizing the subsets of the depth map or the point cloud.

The result of this processing will be a segmentation or classification:
- with a first indicator (label) associated with the mechanical reference corresponding to a first subset of points of the 3D image,
- with a second indicator (label) associated with the target (femur), corresponding to a second subset of points in the 3D image,
- with a third indicator (label) of the background (non-relevant subset of the image).

This processing step will be carried out by successive contour, color and in alternative using trained classifiers, or by artificial intelligence, or by taking into account the geometrical a priori of the positioning of the mechanical reference and the target in relation to the acquisition system.

This step of extracting areas of interest is optional if the matching algorithms applied during the third and fourth steps are sufficiently robust to outliers.

Third step: Matching the Physical Reference Frame Linked to the Target with the Acquisition Reference Frame.

The third step consists in matching the target referential $R_C$ associated to said physical target with the acquisition referential $R_A$, by a registration processing between:
- the subset of the three-dimensional digital image associated with the target, determined in the previous steps, and
- the three-dimensional digital model of the target recorded with the planning data.

This processing consists in determining the $^C T_A$ transformation, giving the position and orientation of the acquisition referential $R_A$ with respect to target referential $R_C$, as shown in FIG. 2.

This processing uses registration techniques to find an underlying deformation common to two geometric structures of the same nature, allowing them to be linked, i.e. attempting to describe the second structure as being obtained from the first by applying a spatial transformation.

The man skilled in the art knows said matching techniques based on the prior extraction of characteristic points, from which deformations are induced, or the exploitation of geometrical structures derived from the original images: points, portions of curves or surfaces obtained by segmentation, insofar as these capture the essential information of the images, whether geometrical—points or lines of strong curvature—or anatomical.

A suitable technique is based on point-to-point registration by means of a process of estimating an optimal transformation between two sets of data, such that their overlapping areas match as well as possible. This can be performed by an algorithm that iteratively aligns the two models by alternating a matching step associating each point of the intraoperative image to its nearest neighbor in the preoperative model, and a transformation estimation step which transforms the intraoperative cloud as to best fit the estimated matches. This process is repeated until the distance between each point of the intraoperative and preoperative model is minimized, below a threshold value.

Registration is said to be rigid if the geometric transformation includes rotation and translation. The registration is said to be non-rigid if the geometric transformation is of higher order (polynomial, splines . . . ) or if the transformation is not parametric.

In the context of the present invention, a rigid registration is generally sufficient to calculate the transformation matrix from the target referential to the virtual referential $R_P$.

Fourth Step: Mapping of the Physical Reference Frame Linked to the Mechanical Reference to the Acquisition Frame.

The fourth step consists in matching the mechanical reference referential $R_M$ associated to the said mechanical reference with the acquisition referential $R_A$, by a registration processing between:
- the 3D image of said mechanical reference, and
- the three-dimensional digital model of said mechanical reference.

The same type of rigid registration processing is applied using the subset of the 3D image points corresponding to the mechanical reference, and its digital representation in the computer memory.

The result of this processing shown in FIG. 3 is used to determine the $^M T_A$ transformation, giving the position and orientation of the mechanical referential $R_M$ relative to acquisition referential $R_A$.

Figure 4:
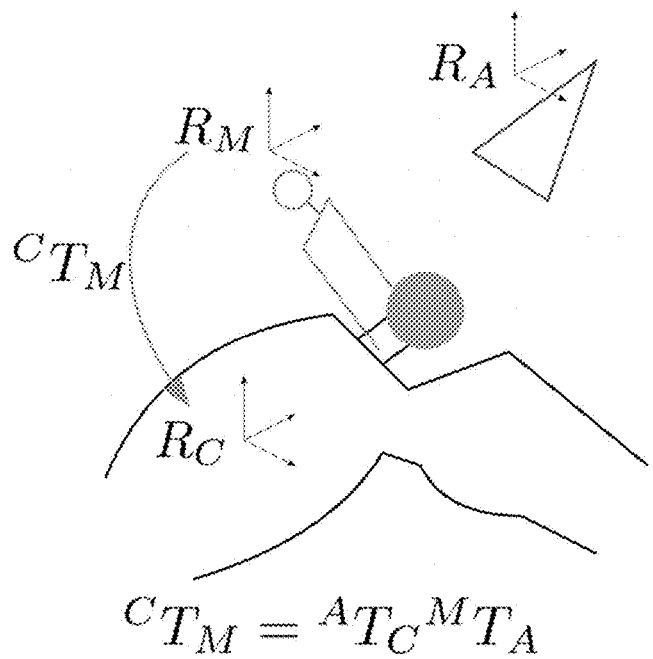
FIG. 4 represents the $^CT_M$ transformation between the mechanical reference and the target is calculated by the composition of the $^AT_C$ (inverse $^CT_A$ matrix) and $^MT_A$ matrices.

Fifth Step: Transformation between Target Referential $R_C$ and Mechanical Referential $R_M$ The fifth step of the process shown in FIG. 4 consists in calculating the transformation between the target referential $R_C$ and the mechanical referential $R_M$. Knowing the $^C T_A$ and $^M T_A$ matrices (shown in FIGS. 2 and 3) thanks to the two previous steps, it is possible to deduce the transformation matrix $^M T_C$ expressing the relation between the target referential $R_C$ and the mechanical referential $R_M$.

Sixth Step: Moving from Initial Planning to Physical Planning

Figure 5:
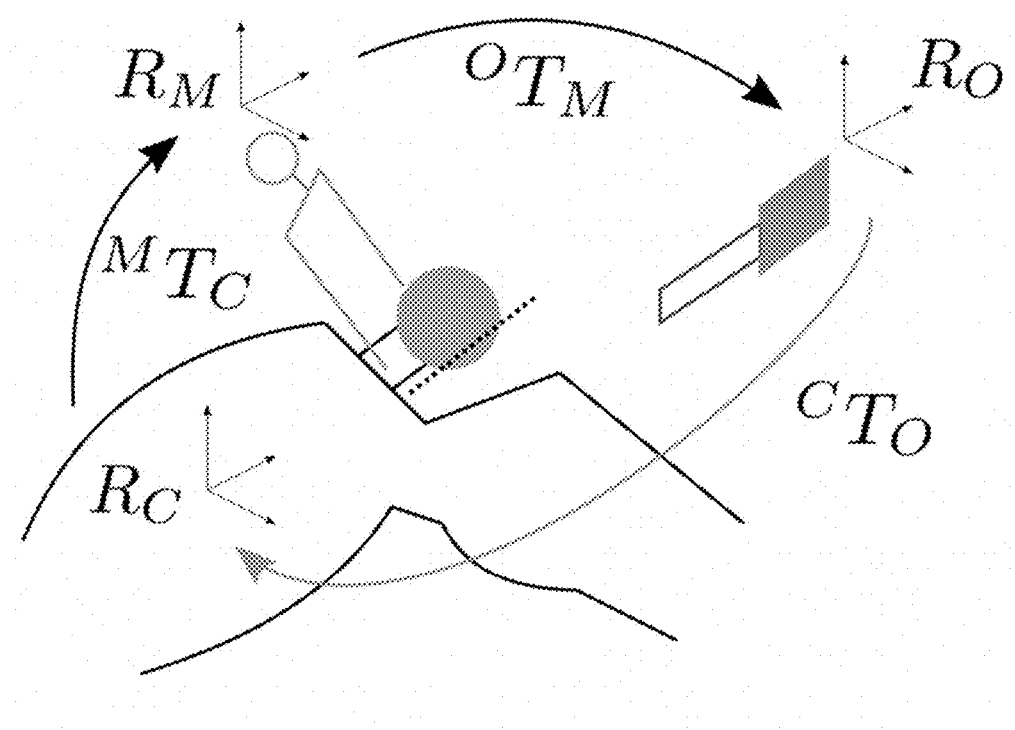
FIG. 5 corresponds to the sixth step of the process. The transformation $^OT_M$, determined from the kinematic chain linking the mechanical reference and the surgical tool, is combined with the transformations $^CT_M$ to calculate $^CT_O$ (the position of the surgical tool in the target and planning referential).

The sixth step represented in FIG. 5 relates to the transposition of the planned action of the initial surgical planning to physical actions performed in the target referential $R_C$ by positioning the tool's support according to the digital planning data thus transposed. The $^O T_M$ transformation, determined using the data obtained from the sensors of the kinematic chain comprising the mechanical reference and the machining tool, is combined with $^M T_C$ to calculate the transformation $^C T_O$ allowing to compute the machining tool position in the target referential, and thus transpose the planning data to the real environment. The knowledge of transformation $^C T_O$ then enables the correction of the machining tool trajectory according to the movements of the target during the intervention.

Surgical planning data, transposed on intraoperative images, can be displayed on a screen 60 in the operating theatre. This provides the surgeon with visual feedback on the progress of the procedure in relation to the schedule.

According to one embodiment steps 2 and 3 are realized without passing through a subset extraction step, by using a single processing using an algorithm robust to outliers, e.g. Random Sample Consensus (RANSAC).

Figure 8:
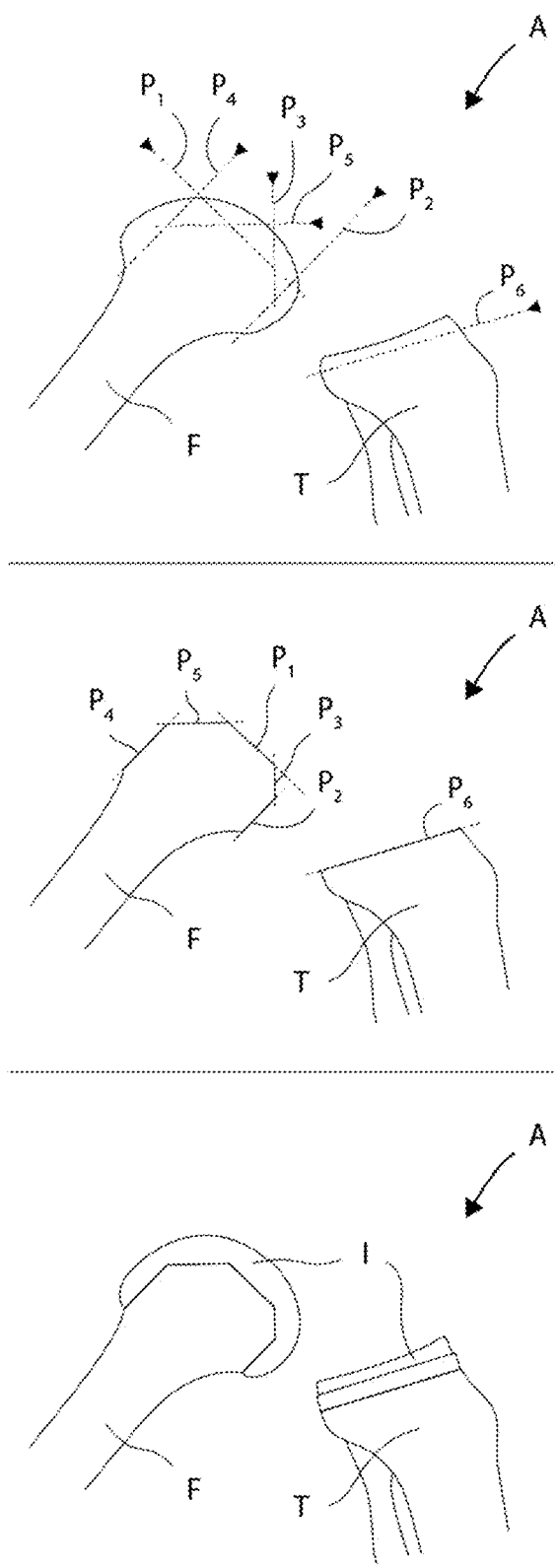
FIG. 8 shows some machining planes $P_1$, $P_2$, $P_3$, $P_4$, $P_5$, $P_6$ for a femur F and a tibia T in view of the implantation of a femoral knee implant I in total knee arthroscopy surgery.

FIG. 8 provides an example of an anatomical structure A which is classically well known for regularly needing surgery, is the knee joint. As known per se, the knee joint includes three bones, the femur F, the tibia T and the patella. (We will intentionally exclude the patella, from this description for it adds no explanatory value) The examples described in the present specification relate therefore to the field of orthopedic surgery and more specifically to the preparation of a femur F and a tibia T for the implantation of a femoral knee implant I.

This preparation according to this example includes a succession of well-known steps, each step being the machining of one of the bones F or T (bone cut using traditionally an oscillating saw) according to a given pre-calculated machining plan $P_1$, $P_2$, $P_3$, $P_4$, $P_5$, $P_6$ (see FIG. 8) comprised in the surgical planning Those machining steps are well-known per se and they usually take place in the same order, depending on the strategy adopted by the operators (surgeons). On FIG. 8, each machining plan $P_1$, $P_2$, $P_3$, $P_4$, $P_5$, $P_6$ is numbered in the generally admitted chronological sequence. Those machining plans $P_1$, $P_2$, $P_3$, $P_4$, $P_5$, $P_6$ are classically determined by a pre-operative surgical planning A pre-operative surgical planning is only valid for one given patient for one given surgery for one given type of implant (size, design, brand, etc.). Each patient (and each surgery) gets a personalized pre-operative surgical planning. Therefore, the machining plans $P_1$, $P_2$, $P_3$, $P_4$, $P_5$, $P_6$ slightly change for each surgery. The usual first step of the pre-operative surgical planning, is to establish a 3D digital model of the target bones F, T. One way to obtain such as 3D digital bones F, T model is to use medical imaging such as computed tomography, X-rays, MRI, fluoroscopy, ultrasound or other imaging means. X-ray or scanner, or even MRI, acquisitions are usually made during full weight-bearing, with typically a frontal (also named coronal or anteroposterior) view, a lateral (or profile) view with the knee in full extension and/or at 20°-30° of flexion, a long-leg view, including the lower limb from the femoral head to the ankle joint and lastly a view of the kneecap at 30° flexion, also called skyline view. From these images it is possible to build a digital model of the bones F, T to be machined during the operation. A particular knee implant I is then selected based on an analysis of the 3D digital bones F, T model.

Figure 6:
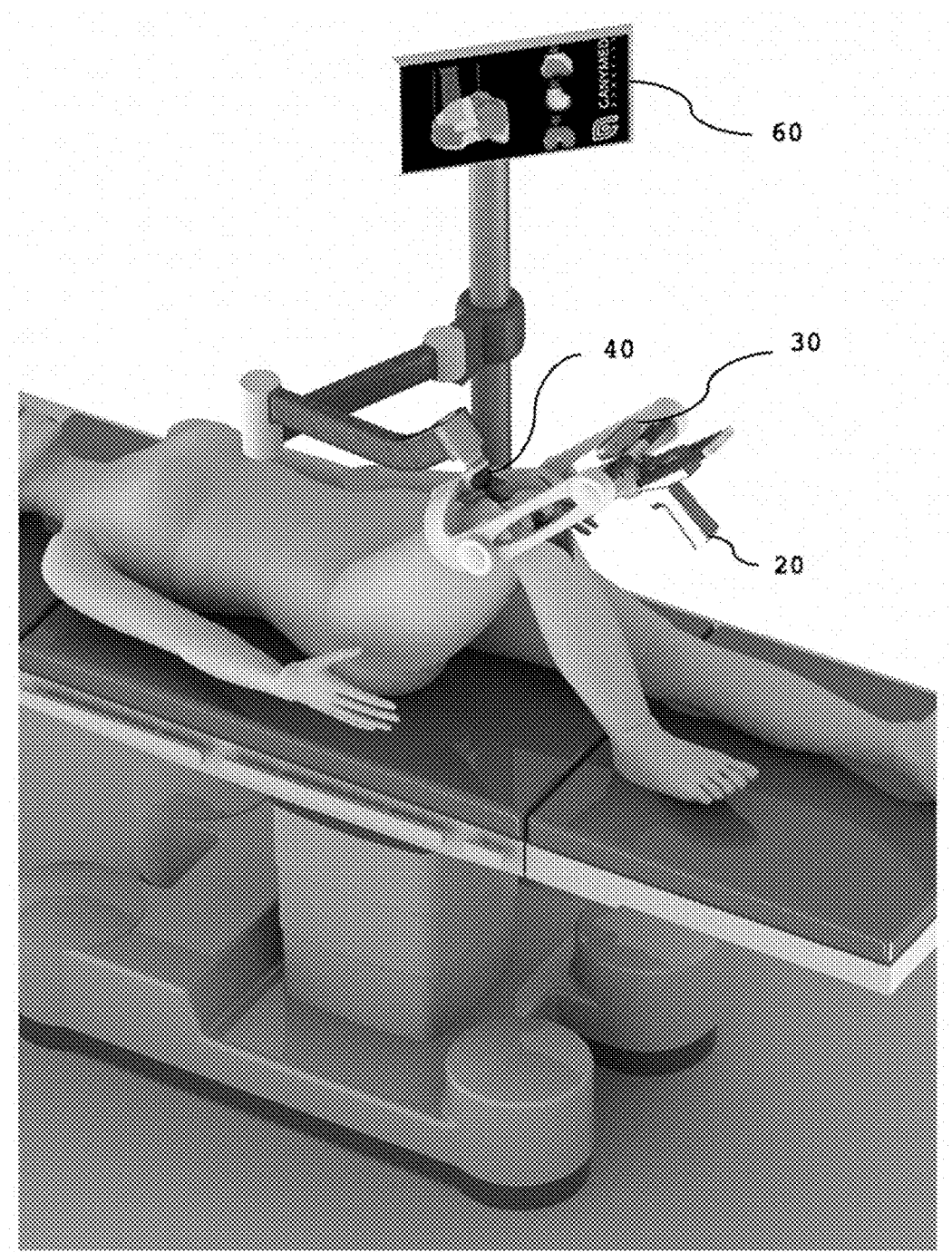
FIGS. 6 and 7 show two examples of how the system and the kinematic chain may be constructed, according to one embodiment where the mechanical reference is kinematically linked to the surgical tool. A human-machine interface, represented here by the screen 60, provides visual feedback on the individual process steps.

The present invention aims at allowing an accurate and safe machining of the bones F, T by means of a surgical device comprising a kinematic chain 70 with a surgical tool 20 as shown in FIG. 6, 7 or 9.

After being established, the F, T bones 3D digital model may be stored in a memory of a control unit of said surgical device.

In one example, the surgical device may include a 3D imaging sensor 30 which its position is well known within the surgical device. This 3D imaging sensor 30 allows the operator, in cooperation with the bones F, T model stored in the memory of the control unit. Once a F, T bones 3D digital model has been determined for a given patient, and stored inside the memory of the control unit, the surgical device, it can be used for surgery. Once the patient is correctly installed, the anatomical structure A to be seen and the surgery device correctly put in place with regards to the patient, at least one 3D image of the anatomical structure A is taken. This 3D image is taken with the 3D imaging sensor 30. The control unit of the surgical device may be configured to perform the step of the method of the present invention. This enables the control unit to position the anatomical structure A with regards to the 3D imaging sensor 30 and therefore to the surgery device. This then enables the control unit to set the precise machining plans $P_1$, $P_2$, $P_3$, $P_4$, $P_5$, $P_6$ for this specific surgery within the target referential $R_A$.

The free surface of the bones F, T to be machined is limited and there are therefore only a few areas where a surgical tool 20 can be put in contact with the bones F, T. This contact has to be as minimally invasive as possible in order to damage neither the bones F, T, nor the surrounding soft tissue while ensuring a precise relative positioning of the surgical tool 20 relative to the bones F, T.

As shown in FIG. 6, 7 or 9, the surgical device aims at machining an anatomical structure A (in this case, a knee) of a patient positioned on an operation table. The patient is usually anesthetized and maintained on the operation table by means of specific and well-known fixation means. In one embodiment illustrated in FIGS. 6 and 7, in addition, the patient's limb in its whole is secured to the kinematic chain 70 of the surgical device.

For example, in addition to the kinematic chain 70 and the surgical tool 20, the surgical device may comprise a base unit aimed at being secured to the operation table and a mechanical reference 40 designed to secure the anatomical structure A. The surgical tool 20 may be configured to be displaced by the operator.

In one embodiment the system for computer guided surgery corresponds to the control unit of said surgical device. Said control unit 80 can for example be a computer. This control unit 80 may comprise a memory, a real time computing element, power supply, power converters, fuses and/or actuators. The control unit 80 may further comprise an operator interface 60 allowing an interaction between the control unit 80 and the operator.

This operator interface 60 may be configured to
   display the images acquired by the 3D sensor and the output of steps one to three
   display real time information such as the surgical tool 20 position relative to the anatomical structure A,
   display the planned implant position and the surgical planning in order to help the operator in choosing the best implant and its position,
   configuring a machining target position of a tool carrier.

The system for computer guided surgery of the present invention may be integrated in the surgical device as control unit as described above or be a processor configured to carry out the steps of the method of the present invention and to communicate to the surgical device by wire connection or wirelessly.

The present invention further comprises a computer program product for computer guided surgery, the computer program product comprising instructions which, when the program is executed by a computer, cause the computer to carry out the steps of the method according to any one of the embodiments described hereabove.

The computer program product to perform the method as described above may be written as computer programs, code segments, instructions or any combination thereof, for individually or collectively instructing or configuring the processor or computer to operate as a machine or special-purpose computer to perform the operations performed by hardware components. In one example, the computer program product includes machine code that is directly executed by a processor or a computer, such as machine code produced by a compiler. In another example, the computer program product includes higher-level code that is executed by a processor or a computer using an interpreter. Programmers of ordinary skill in the art can readily write the instructions or software based on the block diagrams and the flow charts illustrated in the drawings and the corresponding descriptions in the specification, which disclose algorithms for performing the operations of the method as described above.

The present invention further comprises a computer-readable storage medium comprising instructions which, when the program is executed by a computer, cause the computer to carry out the steps of the method according to any one of the embodiments described hereabove.

According to one embodiment, the computer-readable storage medium is a non-transitory computer-readable storage medium.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The invention claimed is:

1. A system for computer guided surgery comprising performing a transposition of an action planned in a virtual environment with respect to a virtual referential $R_p$ to a physical action performed with a surgical tool in a real operating theatre environment for orthopedic surgery of a patient, said surgical tool is fixed to a kinematic chain comprising a sensor unit having at least one sensor configured to follow in real time a spatial configuration of the kinematic chain; said system comprising:
   at least one input adapted to receive at least one 3D image acquired from at least one 3D imaging sensor; said 3D image comprising at least one portion of a target anatomical structure of the patient; and
   at least one processor configured to:
   calculate a transformation $^{C}T_p$ between the virtual referential $R_p$ and a target referential $R_c$ by registration of a digital model of the target anatomical structure with the at least one portion of the target anatomical structure comprised in the 3D image;
   apply the transformation $^{C}T_p$ so as to register said digital model of the target anatomical structure in the target referential $R_c$ so that each point comprised in the digital model of the target anatomical structure has a known position in the target referential $R_c$;
   calculate a transformation $^{C}T_o$ between a referential of the surgical tool $R_o$ and the target referential $R_c$; and apply the transformation $^CT_o$ to the referential of the surgical tool $R_o$ so as to know the position and spatial orientation of the surgical tool in the target referential $R_c$;

so as to know the position and spatial orientation of said surgical tool in both the virtual referential $R_p$ and the target referential $R_c$ in order to reproduce the action planned in the virtual referential $R_p$ in the target referential $R_c$.

2. The system according to claim 1, wherein the at least one processor is further configured to obtain a transformation $^CT_A$ between an acquisition referential of the 3D imaging sensor $R_A$ and the target referential $R_C$ by:
  defining a region of interest in the 3D image comprising said target anatomical structure;
  registering said region of interest comprising the target anatomical structure to the digital model of the target anatomical structure, and
  determining $^CT_A$ from the registration of the digital model of the target anatomical structure with at least one portion of the target anatomical structure comprised in the 3D image.

3. The system according to claim 2, wherein, when the kinematic chain comprises at least one mechanical reference rigidly fixed to the target anatomical structure, and the at least one 3D image comprises at least one portion of the mechanical reference, the at least one processor is further configured to:
  receiving, from the sensor unit of the kinematic chain, data representative of the spatial configuration, in real time, of the kinematic chain;
  calculate a transformation $^OT_M$ between the referential of the surgical tool $R_O$ and the referential of the mechanical reference $R_M$ using the received data;
  calculate a transformation $^MT_A$ between the referential of the mechanical reference $R_M$ and the acquisition referential $R_A$ by matching a digital model of the mechanical reference with the at least one portion of the mechanical reference comprised in the 3D image;
  so that the $^CT_O$ transformation is obtained from the combination of the transformations $^OT_M$, $^MT_A$ and $^CT_A$ between the acquisition referential $R_A$, the mechanical reference referential $R_M$ and the target referential $R_C$.

4. The system according to claim 3, wherein the at least one processor is further configured to use the sensor unit of the kinematic chain to track the movements of the target anatomical structure, rigidly fixed to the at least one mechanical reference, with respect to the surgical tool, so that whenever a deviation in the position and/or spatial orientation of the target anatomical structure is detected, the transposition of the planned actions from the virtual environment to the real environment is corrected for said deviation.

5. The system according to claim 2, wherein the at least one 3D imaging sensor being fixed to the kinematic chain, the at least one processor is further configured to calculate a transformation $^AT_O$ between the referential of the surgical tool $R_O$ and the acquisition referential of the 3D imaging sensor $R_A$ from data obtained from the sensor unit of the kinematic chain so that the $^CT_O$ transformation is obtained from the combination of the transformation $^AT_O$ and the transformation $^CT_A$ between the acquisition referential $R_A$ and the target referential $R_C$.

6. The system according to claim 5, wherein the 3D imaging sensor fixed on the kinematic chain moves along a known trajectory and multiple 3D images are acquired along the trajectory, the at least one processor is further configured to jointly process multiple 3D images acquired along the trajectory so as to use multiple 3D images for the registration with the digital model of the target anatomical structure.

7. The system according to claim 5, wherein the at least one processor is further configured to track the movements of the target anatomical structure with respect to the surgical tool using the 3D imaging sensor and a visual tracking algorithm, so that whenever a deviation in the position and/or spatial orientation of the target anatomical structure is detected, the transposition of the planned actions from the virtual environment to the real environment is corrected for said deviation.

8. The system according to claim 1, wherein said kinematic chain consists of a deformable structure comprising multiple rigid elements connected by joints and said kinematic chain further comprises sensors for measuring the forces applied to its elements.

9. The system according to claim 1, wherein the acquisition of the 3D image received by the at least one input is carried out using at least two sensors and a projector to carry out an acquisition by stereovision or structured light.

10. The system according to claim 1, wherein the three-dimensional digital model of the target anatomical structure is generated using 2D X-ray radiographies comprising the target anatomical structure, a statistical shape model of the target anatomical structure and/or the 3D image acquired intraoperatively by the 3D imaging sensor.

11. The system according to claim 1, wherein the three-dimensional digital model of the target anatomical structure is digitally modified to simulate measurement noise or the presence of cartilage, said modifications being calculated from training data or biomechanical simulation data.

12. The system according to claim 1, wherein registration of the digital model of the target anatomical structure with the at least one portion of the target anatomical structure comprised in the 3D image is a non-rigid transformation.

13. A computer-implemented method for guiding a surgical tool in a real operating theatre environment suitable for orthopedic surgery of a patient, said surgical tool is fixed to a kinematic chain comprising a sensor unit having at least one sensor configured to follow in real time a spatial configuration of the kinematic chain; said method comprising:
  receiving of at least one 3D image acquired from at least one 3D imaging sensor; said 3D image comprising at least one portion of a target anatomical structure of the patient;
  calculating a transformation $^CT_p$ between a virtual referential $R_p$ and a target referential $R_c$ by a registration of a digital model of the target anatomical structure with the at least one portion of the target anatomical structure comprised in the 3D image;
  applying the transformation $^CT_p$ so as to register said digital model of the target anatomical structure in the target referential $R_c$ so that each point comprised in the digital model of the target anatomical structure has a known position in the target referential $R_c$;
  calculating a transformation $^CT_o$ between a referential of the surgical tool $R_o$ and the target referential $R_c$; and
  applying the transformation $^CT_o$ to the referential of the surgical tool $R_o$ so as to know the position and spatial orientation of the surgical tool in the target referential $R_c$;
  so as to know the position and spatial orientation of said surgical tool in both the virtual referential $R_p$ and the target referential $R_c$ in order to reproduce an action planned in the virtual referential $R_p$ in the target referential $R_c$.

14. The method according to claim 13, further comprising obtaining a transformation $^CT_A$ between an acquisition referential of the 3D imaging sensor $R_A$ and the target referential $R_C$, by:
  defining a region of interest in the 3D image comprising said target anatomical structure;
  registering said region of interest comprising the target anatomical structure to the digital model of the target anatomical structure; and
  determining $^CT_A$ from the registration of a digital model of the target anatomical structure with the at least one portion of the target anatomical structure comprised in the 3D image.

15. The method according to claim 14, wherein the kinematic chain comprises at least one mechanical reference rigidly fixed to the target anatomical structure and the at least one 3D image comprises at least one portion of the mechanical reference; the method further comprises:
  receiving, from the sensor unit of the kinematic chain, data representative of the spatial configuration, in real time, of the kinematic chain;
  calculating a transformation $^OT_M$ between the referential of the surgical tool $R_O$ and the referential of the mechanical reference $R_M$ using the received data;
  calculating a transformation $^MT_A$ between the referential of the mechanical reference $R_M$ and the acquisition referential $R_A$ by matching a digital model of the mechanical reference with the at least one portion of the mechanical reference comprised in the 3D image;
  so that the $^CT_O$ transformation is obtained from the combination of the transformations $^OT_M$, $^MT_A$ and $^CT_A$ between the acquisition referential $R_A$, mechanical reference referential $R_M$ and the target referential $R_C$.

16. The method according to claim 15, wherein the movements of the target anatomical structure with respect to said surgical tool are tracked by the sensor unit of the kinematic chain so that whenever a deviation in the position and/or spatial orientation of the target anatomical structure is detected, the transposition of the planned actions from the virtual environment to the real environment is corrected for said deviation.

17. The method according to claim 14, wherein the at least one 3D imaging sensor is fixed to the kinematic chain the method further comprises calculating a transformation $^AT_O$ between the referential of the surgical tool $R_O$ and the acquisition referential of the 3D imaging sensor $R_A$ from data obtained from the sensor unit of the kinematic chain so that the $^CT_O$ transformation is obtained from the combination of the transformation $^AT_O$ and the transformation $^CT_A$ between the acquisition referential $R_A$ and the target referential $R_C$.

18. The method according to claim 17, wherein the 3D imaging sensor fixed on the kinematic chain moves along a known trajectory and multiple 3D images are acquired along the trajectory, the method further comprises jointly processing multiple 3D images acquired along the trajectory so as to use multiple 3D images for the registration with the digital model of the target anatomical structure.

19. The method according to claim 17, wherein the movements of the target anatomical structure with respect to said surgical tool are tracked by the 3D imaging sensor a visual tracking algorithm, so that whenever a deviation in the position and/or spatial orientation of the target anatomical structure is detected, the transposition of the planned actions from the virtual environment to the real environment is corrected for said deviation.

20. A computer-readable storage medium comprising instructions which, when executed by a computer, cause the computer to carry out the method according to claim 13.

* * * * *